United States Patent [19]

Higo et al.

[11] Patent Number: 5,055,408
[45] Date of Patent: Oct. 8, 1991

[54] AUTOMATED IMMUNOASSAY ANALYSER

[75] Inventors: Yuji Higo, Aichi; Hidechika Hayashi, Kanagawa; Shuji Iwasaki, Tokyo, all of Japan

[73] Assignee: Toyo Soda Manufacturing Co., Ltd., Shinnanyo, Japan

[21] Appl. No.: 590,530

[22] Filed: Sep. 28, 1990

Related U.S. Application Data

[63] Continuation of Ser. No. 394,150, Aug. 14, 1989, abandoned, which is a continuation-in-part of Ser. No. 901,300, Aug. 28, 1986, abandoned.

[30] Foreign Application Priority Data

Aug. 30, 1985 [JP] Japan .................. 60-191126
Jul. 7, 1986 [JP] Japan .................. 61-159473

[51] Int. Cl.$^5$ .......................................... G01N 35/02
[52] U.S. Cl. .................................... 436/48; 436/49; 436/809; 422/65; 422/71; 422/73; 422/100; 435/301; 141/130
[58] Field of Search ............. 422/63, 65, 71, 73, 422/100; 436/47–79, 809; 435/239, 300, 301; 141/130

[56] References Cited

U.S. PATENT DOCUMENTS

| | | | |
|---|---|---|---|
| 3,015,415 | 1/1962 | Marsh et al. | 222/383 |
| 3,213,903 | 10/1965 | Armstrong | 222/72 |
| 3,684,452 | 8/1972 | Bessman | 422/64 |
| 4,265,855 | 5/1981 | Mandle et al. | 422/65 |
| 4,276,258 | 6/1981 | Ginsberg et al. | 422/64 |
| 4,287,155 | 9/1981 | Tersteeg et al. | 422/64 |
| 4,647,432 | 3/1987 | Wakatake | 422/67 X |
| 4,670,219 | 6/1987 | Nelson et al. | 422/63 |
| 4,681,742 | 7/1987 | Johnson et al. | 422/100 |
| 4,727,033 | 2/1988 | Hijikata et al. | 422/65 |

FOREIGN PATENT DOCUMENTS

85168 5/1983 Japan .................. 422/65

Primary Examiner—Robert J. Warden
Assistant Examiner—Lynn M. Kummert
Attorney, Agent, or Firm—Oblon, Spivak, McClelland, Maier & Neustadt

[57] ABSTRACT

An automated immunoassay analyzser comprising a transfer route on which test plates each having a plurality of chambers for immunological reaction opened upwards are transferred continually with a constant interval of time, and devices of at least A, B, C and D described below which are arranged on the transfer route from upstream to downstream in the order referred to in which the device A is for injecting the sample comprising a vertically and horizonally driven support, a pipet fixed to the support, and a nozzle tip usable for a single sample and removably attached to the lower end of the pipet, the device B is for B/F separation and the device C is for injecting the substrate solution and both devices are integratedly combined and comprise a vertically and horizontally driven support, a washing tube supported by the support, a temperature controllable solution reservoir block fixed to the support, a substrate injection tube provided to the lower side of the reservoir block, the washing tube and the substrate solution injection tube being arranged in alignment and spaced each other according to the pitch of the cup arrangement, and the device D is for photometry with which to measure optically detectable changes caused in the substrate in the chamber of immunological reaction.

6 Claims, 14 Drawing Sheets

AUTOMATED IMMUNOASSAY ANALYSER

This application is a continuation of application Ser. No. 07/394,150, filed on Aug. 14, 1989, now abandoned, which is a continuation of Ser. No. 06/901,300, filed on Aug. 26, 1986, now abandoned.

BACKGROUND OF THE INVENTION

FIELD OF THE INVENTION

The present invention relates to an automated immunoassay analyzer for assaying a number of test samples automatically and continuously.

Detection of a minute amount of biological substances by an immunological procedure, such as those embodied as diagnosis kit, has received a wide attention and attempts are being made to develop it. Since the test procedure is simple and tiresome, it is difficult for an operator to treat many minute samples and reagents with a high precision for a long time. Possibility of human errors due to different operators and an insufficient number of operators for the rapidly increasing number of samples to be tested has accelerated the need for automatizing the test apparatus for immunological reactions.

Processes for immunological procedures are different for different labels; thus, they include FIA using a chemical fluorescent material, RIA using a radioactive substance and EIA using an enzyme, each as the label. Therefore, in automatizing these test systems, the constitution and assembly of the apparatus must be adapted to the particular properties of the respective immunological reactions and the labels, and furthermore convenience in practical use and the cost of operation should also be taken into consideration.

SUMMARY OF THE INVENTION

The present invention has been made from the standpoint mentioned above, and provides an automated immunoassay analyzer that is suitable to an enzymatic immunoassay system using an enzyme as label in which is measured the amount of change detectable by an optical means that occurs on a substrate as a result of the enzymatic activity.

Another object of this invention is to provide an automated analyzer with which a number of test samples can be continuously and effectively treated for the measurement.

DETAILED DESCRIPTION OF THE INVENTION

The analyzer of the present invention which has been made to attain the objects mentioned above comprises a transfer route on which test plates each having a plurality of chambers for immunological reaction opened upwards are transferred continually with a constant interval of time, and devices of at least A, B, C and D described below which are arranged on the transfer route from upperstream to downstream in the order referred to:

A: a device for injecting samples to be assayed into the chamber of immunological reactions, B: a device for the (Bound/Free) separation for removing reaction residue in the chamber of immunological reactions, C: a device for injecting a substrate solution into the chamber of immunological reactions, and D: a device for photometry with which to measure optically detectable changes caused in the substrate in the chamber of immunological reactions.

The outline of the treating system in the enzymatic immunoassay at which the analyzer of the present invention aims somewhat differs depending on which of the sandwich or the competition methods is applied and which of the antigen or the antibody is measured. In this context, the sandwich method to measure the antigen is explained, though there is no essential difference from other methods.

Generally speaking, the process consists of several stages of operation. In the first stage, an antibody which is already fixed on the surface of an insoluble carrier is made to react with and an antigen in a particular sample is reacted into a solidified antibody-antigen-enzyme labelled antibody complex. In the second stage of operation, the complex which is combined with the insoluble carrier is left in the immunological reaction chamber and the sample in excess is removed by the, so-called, B/F separation. In the third stage of operation, a substrate solution is added to the above-mentioned complex to effect the enzymatic activity. Finally in the fourth stage of operation, either at the same time or independently of the enzymatic activity applied to the substrate in the third stage, a change appearing in the substrate is photometrically measured (for example when a substrate, 4-methylumbelliferyl phosphoric acid monoester is decomposed by the action of an enzyme, alkaline phosphatase, the product of 4-methylumbelliferone is detected by the fluorescent emission). More particularly, the first stage of operation requires preparation of a vessel provided with a cell (or a reaction chamber) which contains a certain antibody selected according to the test item and affixed on the surface of an insoluble carrier, injection of a sample into the cell, and injection of an enzyme-labelled antibody at the same time or independently of the sample injection (or otherwise, the enzyme-labelled antibody may be added beforehand in the cell); these operations require to be carried out successively with a predetermined timing.

In this connection, the present invention adopts the analyzer having said constitution which is capable of continuous and automatic treatment in immunoassay by using cells (reaction chambers) opened upwards, and by transferring a test plate having the cells on it on a transfer route intermittently with a predetermined interval of time to perform appropriate treatment while the cells are stopped at an appropriate position.

Using the constitution of the analyzer and setting an adequate timing of intermittent transfer of the test plates, a plurality of test plates can be automatically transferred, treated in each stage of operation and measurement with a continuous and consistent manner.

The timing for the intermittent transfer is determined by considering the time required in the stage of the longest time of treatment as criteria among stages of operation arranged successively along the route of transfer. The amount of substances intermittently transferred is determined usually from the interval of reaction chambers on the test plate.

The test plate employed in this invention may be a known type of multi-titre plate or one having many holes each of which can incorporate a test cup for the reaction chamber. Especially the latter test plate has an advantage in that different kinds of antibodies selected according to the test items of the test samples are placed in as many test cups and the cups are more easily arranged in the order of tests.

The transfer route usually composes, for example, of a flat transfer plane of a certain length on which a test plate slides and a transfer mechanism of the test plate (such as a rotary belt or a cam mechanism) which carries and moves the test plate intermittently and successively with a certain interval of time. In addition, it is preferable to assemble an appropriate thermostat along the transfer route to maintain an appropriate temperature for the immunological and enzymatic reactions.

The devices to be installed along the transfer route successively downstream are required to contain at least devices A–D described before.

The first device A, a sample injection device, is a micropipet for adding a predetermined amount of a sample solution either to a cup containing a predetermined antibody fixed to an insoluble carrier (for example a bead in a test cup) or to another cup containing an enzyme-labelled antibody.

Preferably the micropipet scans in the lateral direction (a direction perpendicular to the direction of transfer) on the plurality of test cups which are placed in the lateral direction. When an enzyme-labelled antibody is injected separately, the injection device is placed next to the sample injection device.

After the sample has been injected as above, the cell or test cup is incubated for a predetermined time.

The second device B for the B/F separation is used for washing the cell and removing the reaction residue. Generally a washing solution is introduced via a wash nozzle into the cell and withdrawn through a suction nozzle. The introduction and suction of the washing solution should better be repeated alternatively at several times.

The third device C for injecting a substrate is used for injecting a substrate solution to a cell in which a solidified antibody-antigen-enzyme labelled antibody complex is fixed on the surface of an insoluble carrier. For this end, a general purpose liquid injection apparatus may be employed.

The fourth device D is for measuring, for example, absorbance or fluorescence intensity. When a test plate having cells in several lateral rows, as a suitable example of this invention, is used, a photometric device is preferably used for each raw of cells. Thus, the photometric procedure which is relatively time-consuming and, at the same time, rate-controlling in determining the timing of the intermittent transfer of the test plate can be made more effective, hence the overall effectiveness of the whole photometric procedure can be improved.

The present invention will be more clearly understood from the following description of preferred embodiments with reference to the accompanying drawings.

DETAILED DESCRIPTION OF THE PREFERRED EMBODIMENTS

Figure 1A:
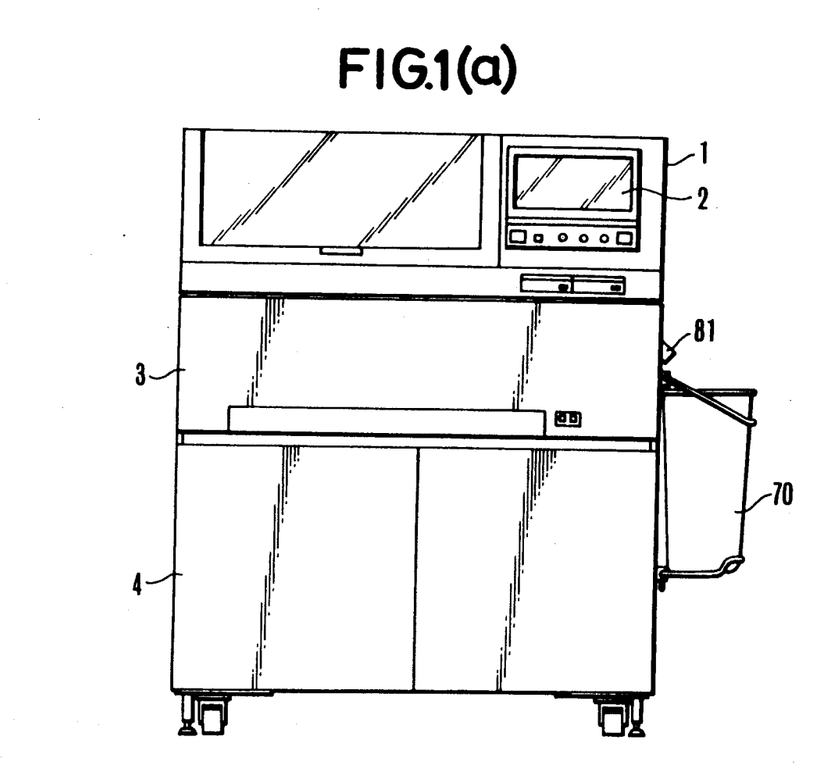
FIGS. 1(a) and 1(b) are respectively an outlook of an example of analyzer according to the present invention.
Figure 1B:
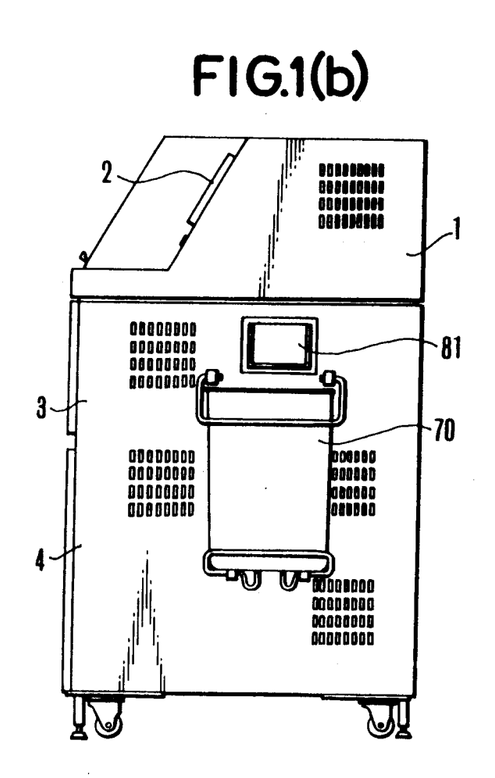

FIGS. 1(b) show an example of the extension of the enzymatic immunoassay analyzer. In the figures, 1 is the measuring part where the system proper including the transfer route is contained, on which front the operational panel 2 is provided. The part 3, located beneath the measuring part 1, is the test cup storing part in which test plates are elevated to and descend from the part 1 by elevators described below. The part 4 is a storage area where a mechanism to control the whole system, power source and reagent solutions in bottles are stored. On the side wall is found a basket 70 to discard used test cups.

Figure 2:
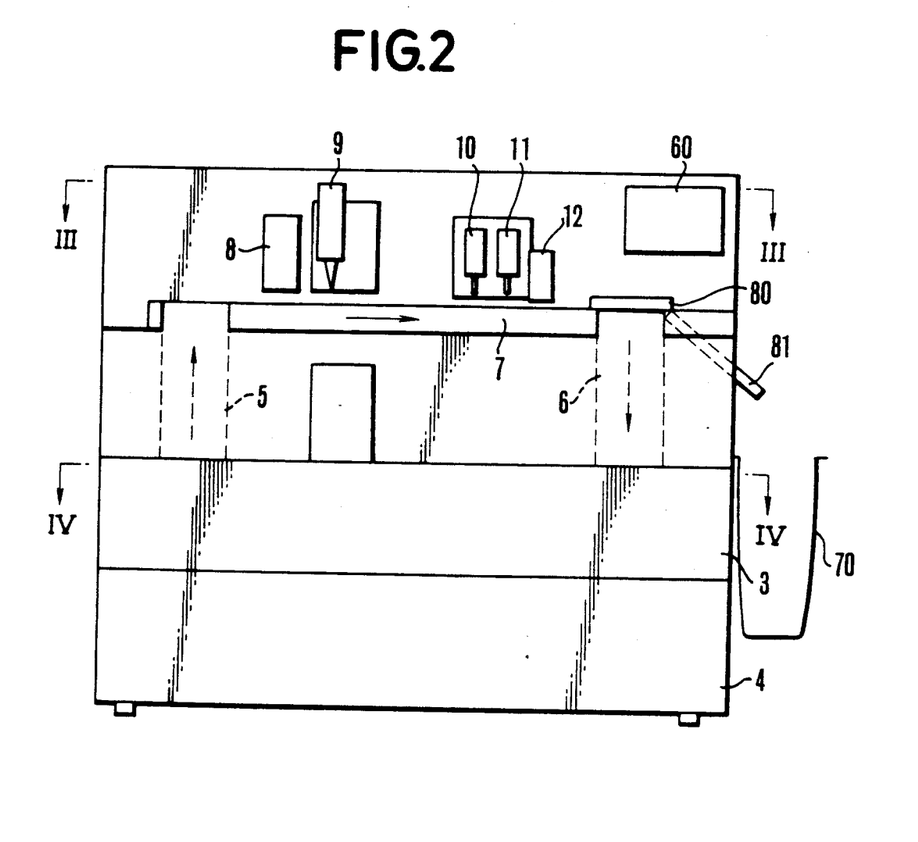
FIG. 2 is a front view schematically showing the inner constitution of the measuring part of the analyzer.
Figure 3:
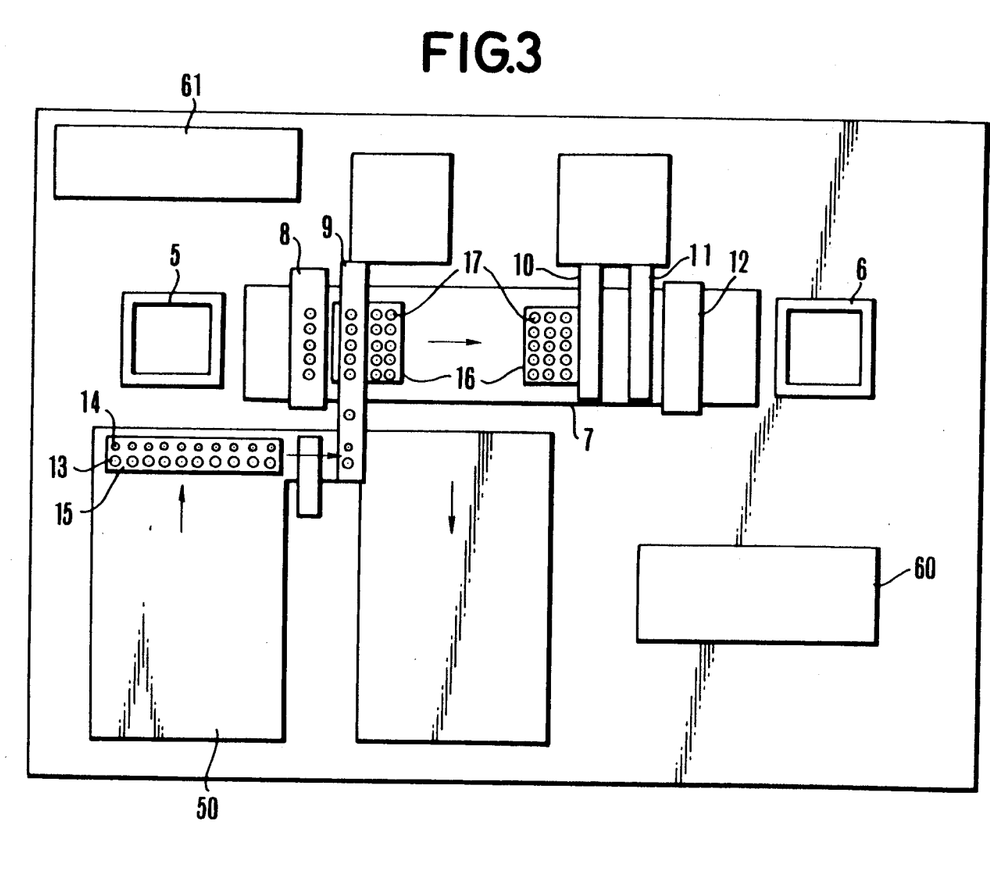
FIG. 3 is a schematic view of the constitution on the cross section taken along a line III—III of FIG. 2.

FIGS. 2 and 3 are respectively schematic front and top views of the inner constitution of the measuring apparatus. A pair of elevators (mechanism itself is not shown in the figures) include two shafts 5 and 6, and between them is a transfer route 7. Above the upper side of the transfer route 7 are located, from upperstream to downstream, a seal breaking device 8 which tears by pressure the seal of upper opening of each test cup, a sample injection device 9, a B/F separation and washing device 10, a device for injection of a substrate solution 11, a device for measuring fluorescence intensity 12, and a test cup disposer 80, with appropriate intervals in between.

In FIG. 3, 50 is a sample loader, a cup holder 15 contains a sample cup 13 and a nozzle tip 14 for each test sample and is sent in the direction shown by an arrow. The nozzle tip mentioned is subsequently connected to a nozzle and a constant volume of sample is injected to each test sample in a predetermined test cup. The procedure is controlled to repeat the operation for each test sample in the specified order. In the figure, 16 is a test plate and 17 is a test cup.

Figure 4:
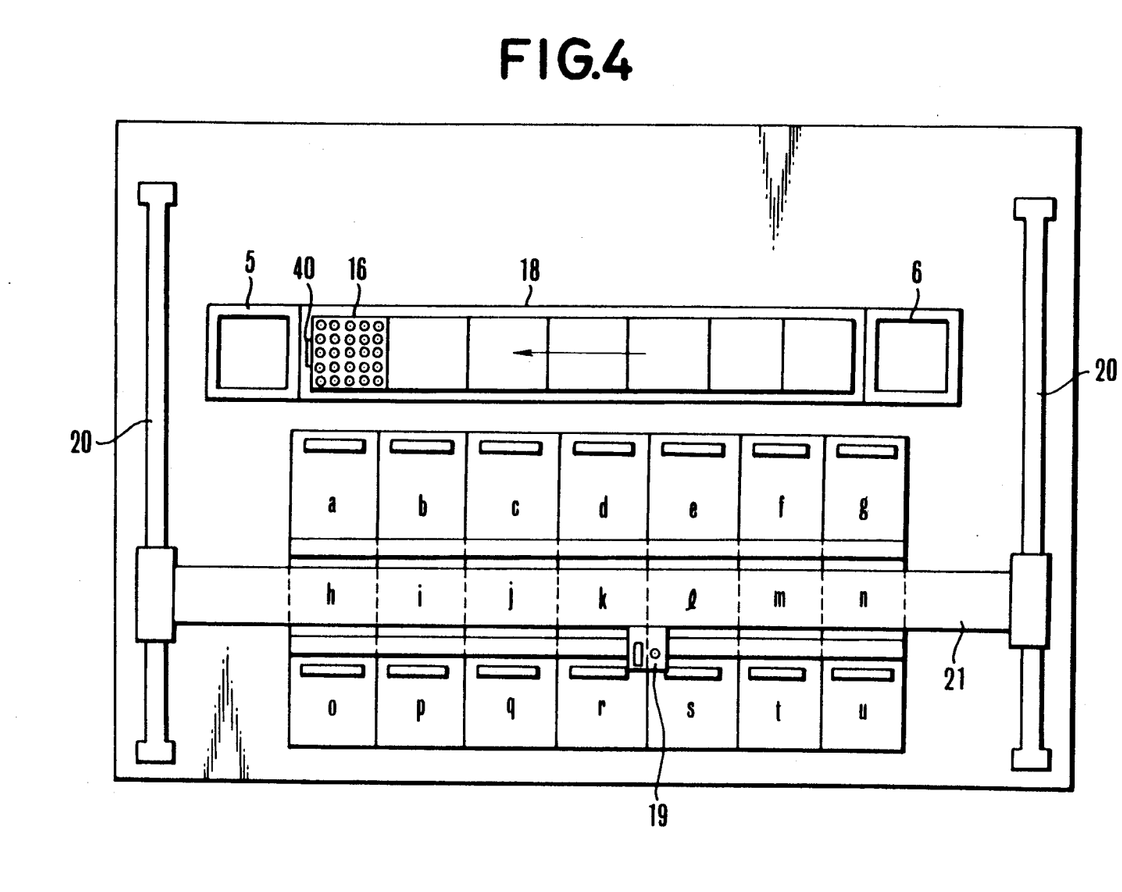
FIG. 4 is a schematic view of the constitution on the cross section taken along a line IV—IV of FIG. 2.

FIG. 4 is a plan view schematically showing the inner constitution of the test cup storage 3. Along a transfer route 18 settled between the bottoms of the two elevator mechanisms 5 and 6, an empty test plate 16 is transferred. A pick-up device 19, which can move as desired in any x and y position by the aid of the supporting plate 21 and a pair of rails 20, takes up a certain test cup from the test cup shelves a - u which store test cups in a regulated manner and place the cup in the determined position on the test plate 16. All the procedures necessary to complete the test plate 16 are performed before the test plate arrives at the up-going elevator 5. A stopper 40 is provided on the test plate 16 for the purpose of stopping it on the transfer route 18. The stopper projects upwards above the transfer route by a driving mechanism (not shown in the figure) in order to get out of the transfer route when necessary, for instance when timing is adjusted for loading the test cups and transferring them to the elevator 5.

The procedure mentioned above may be controlled with a control mechanism provided by a microcomputer. Thus, in FIGS. 2 and 3, a main controller module 60 which is incorporated in a microcomputer works to control all the driving mechanisms in the whole system and input signals from the panel, and to display scheduled data. A subcontroller module 61, also incorporated in the microcomputer, controls every driving mechanism according to signals delivered from the main controller module 60. The outline of the procedure (or the work of the whole system of the analyzer) operated by the controller modules 60 and 61 is indicated by a block diagram shown in FIG. 5(a).

Figure 5A:
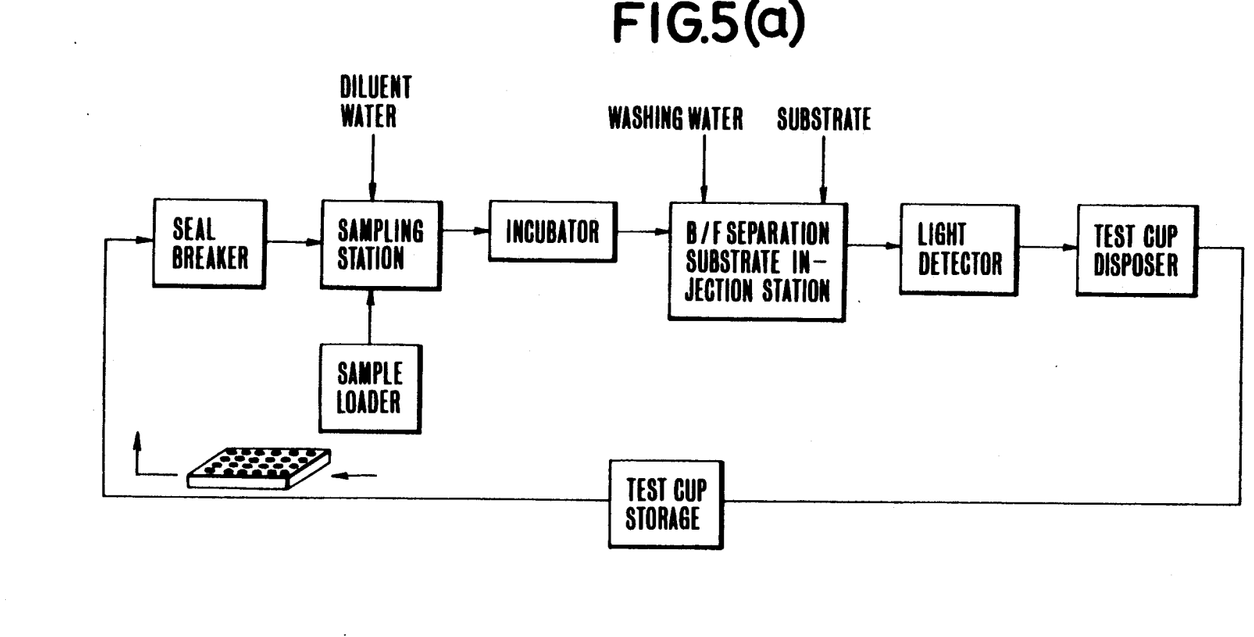
FIG. 5(a) is a block diagram to explain functions of the whole analyzer and FIG. 5(b) simply explains the control system.
Figure 5B:
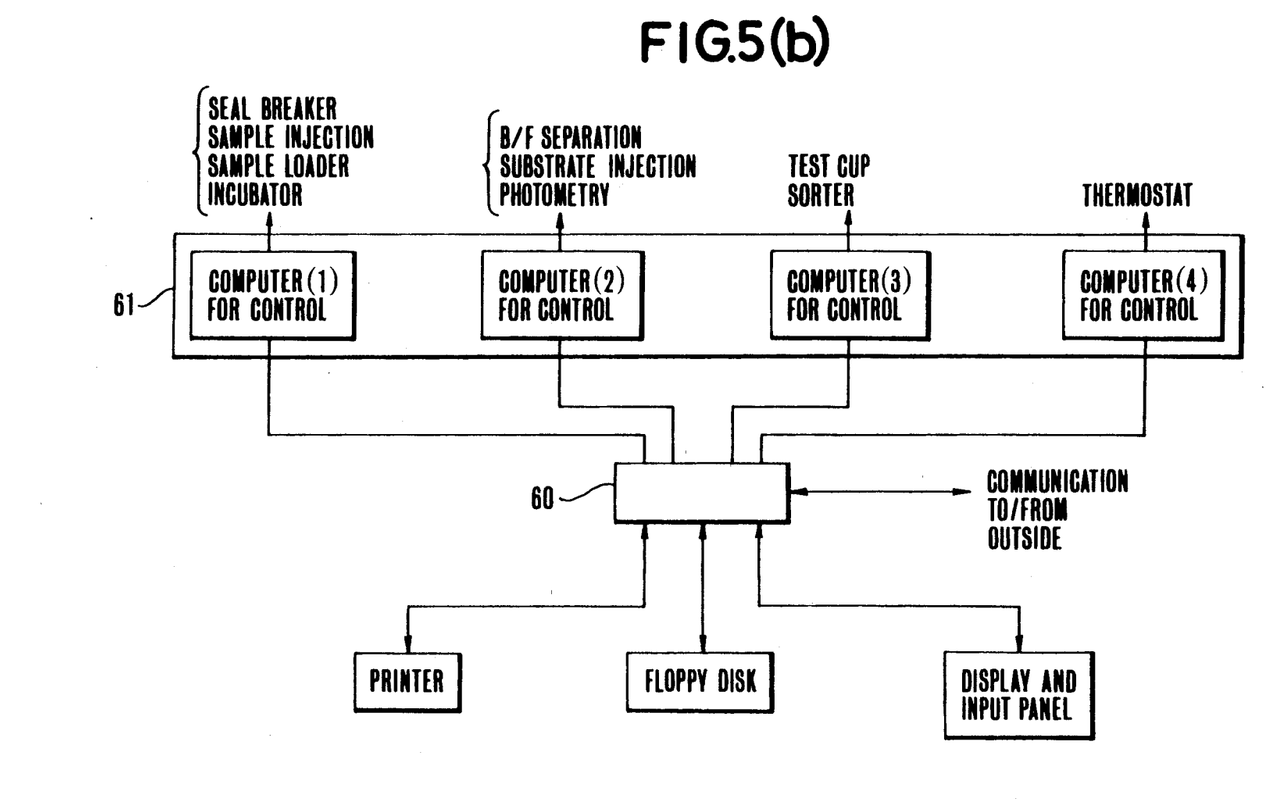

FIG. 5(b) schematically shows the system with which the analyzer of this invention is controlled by the main- and sub-controller modules mentioned above. The order of measurements is given from the input panel (or from readout of memory stored in a floppy disk) and the estimation of the prescribed items is carried out according to the given order.

Figure 6:
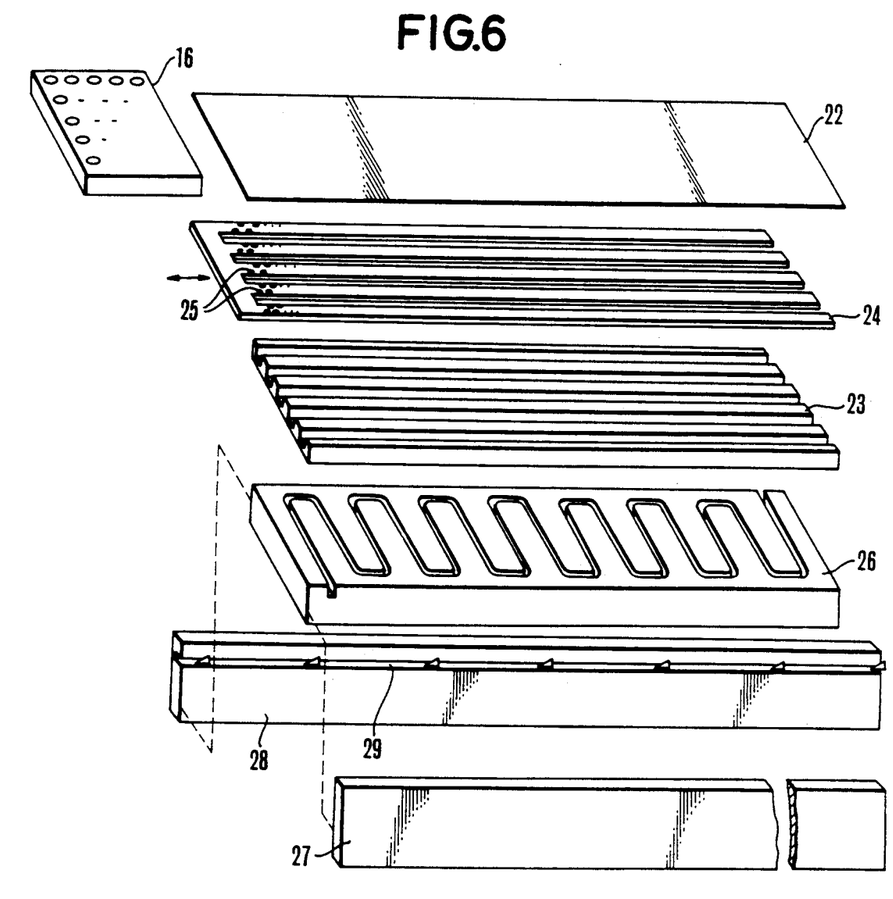
FIG. 6 is a development of constitution at the transfer route.

FIG. 6 is an exploded view of the structure of the transfer route 7. The transfer route consists of an upper cover 22 forming a transfer plane, a magnet holder 23 which is closely attached to the bottom of the upper cover 22 and has a plurality of grooves extending in the longitudinal direction, a joined assembly of magnetic bars 24 which fit to the grooves on the magnet holder 23 and are driven so as to move alternatingly in the longitudinal direction and have a number of pieces of magnet 25 on the upper surface, a thermostatic plate 26 closely attached to the bottom surface of the magnet holder 23, and side plates 27 and 28 which support the multilayer structure. On one of the side plates 28 is incorporated a test plate transferring bar which will be described later more in detail.

The magnetic bases 24 are used for generating, via the magnets 25, an oscillating magnetic field (usually of 0.1–10, preferably 0.5–5 Hz) which acts on the magnetic beads 34 in test cups for the purpose of agitation and improving the accuracy and precision of photometry. In the figure, the thermostatic plate 26 has a snake-like bent groove in which thermostated water is circulated to maintain a constant temperature. But a different embodiment of this invention can be realized, if a flat heater is placed on the lower side of this plate 26 or on the interface between the magnetic plate 23 and this plate 26, and the temperature is sensed with a temperature sensor placed on this plate 26.

Figures 7, 8:
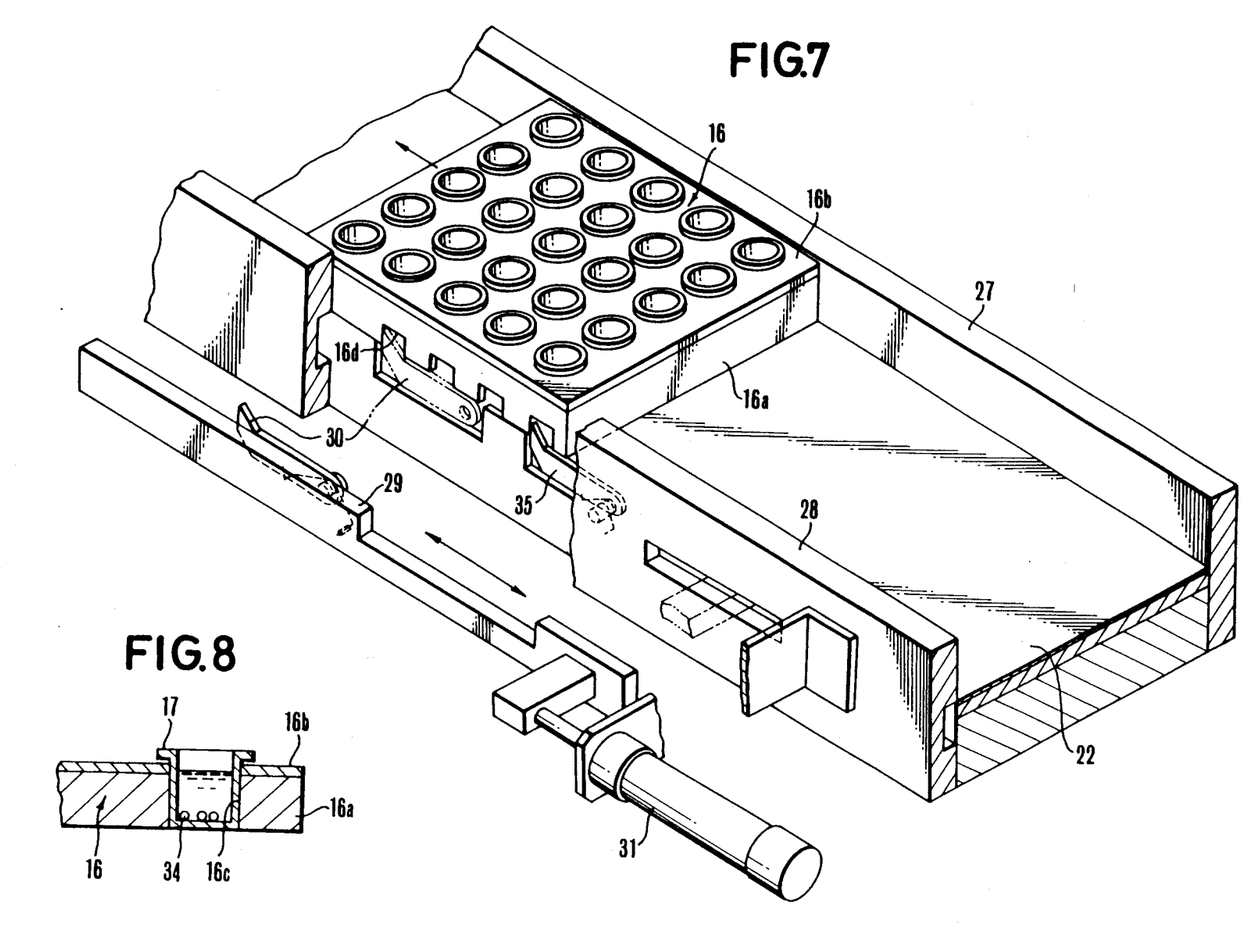
FIG. 7 is a partial slant view provided for explanation of the transfer route for test plates.
FIG. 8 is a partial cross section of the test plate.
Figure 9:
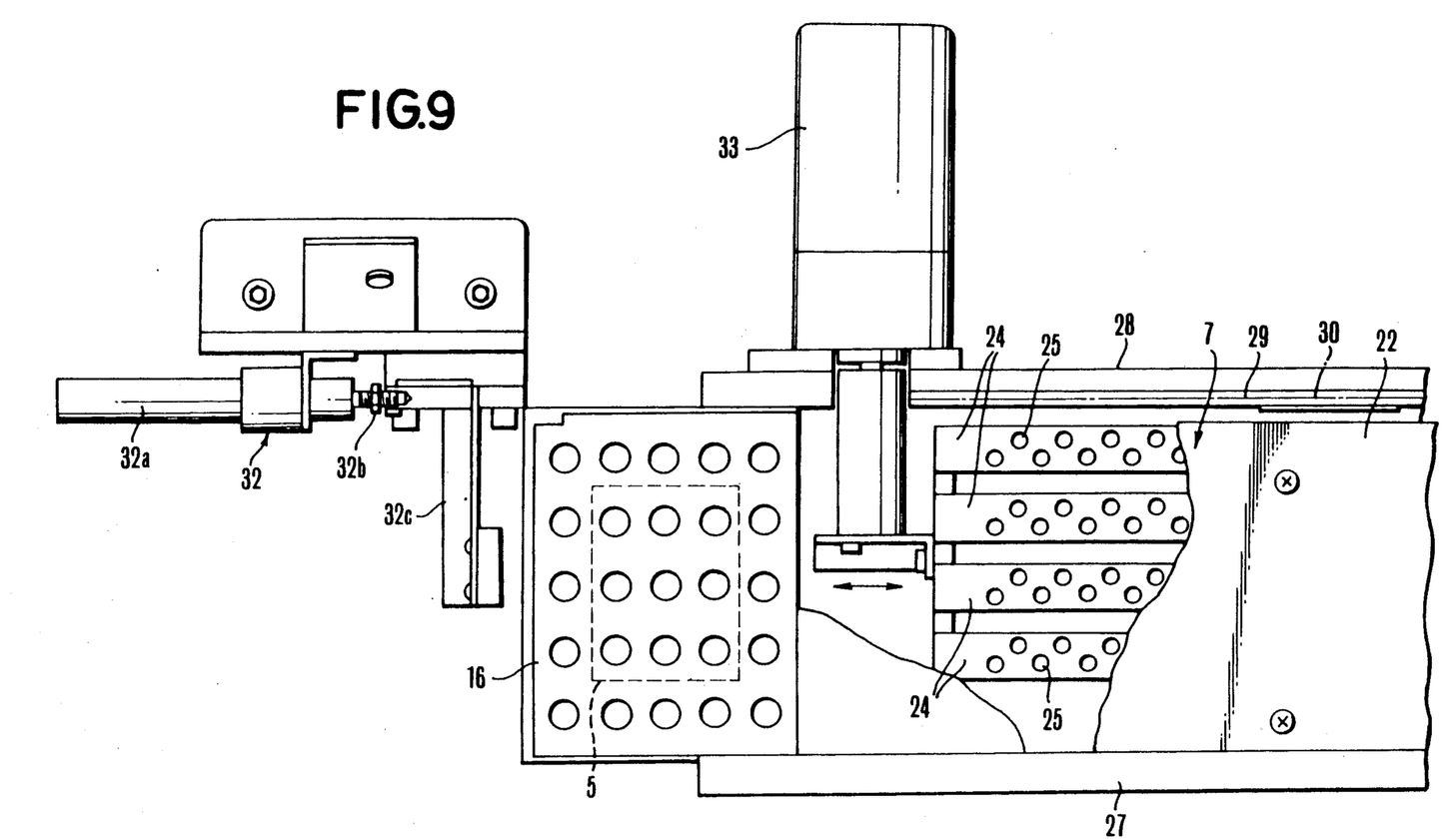
FIG. 9 is a detailed plan view of the transfer route in its upperstream.

FIGS. 7 and 9 show the test plate 16 mounted on the transfer route 7 and the mechanism of transference. The test plate 16 consists of an aluminum base 16a and a thin plate 16b of vinyl chloride coating the base 16a to suppress the heat dissipation. There are drilled a plurality of holes 16c (FIG. 8) which penetrate the test plate 16 in the vertical direction and each fits a test cup 17. Further, on the side of the test plate 16 facing the side board 28 are formed saw-teeth shaped ratchet teeth 16d arranged with a constant pitch, as are seen in FIG. 7, in which teeth fit upwardly based ratchet nails 30 on a transferring bar 29 which is slidingly connected with the side board 28 and reciprocates along a constant length. The transferring bar 29 is constructed to reciprocate within a certain length via an air cylinder 31 (or an eccentric cam arrangement as an alternative). Thus, the ratchet nails 30 fit the ratchet teeth 16d on the test plate 16, to move the plate 16 on the surface of the transfer cover 22 and to transfer it intermittently in the direction shown by an arrow. The ratchet nails 30 are of course connected with the transferring bar 29 by an adequate interval.

The upwardly based nail 35 is for preventing the test plate 16 from being transported in the reverse direction. The nail is fixed on the side board 28 laterally of the transferring bar 29 and fits the ratchet 16d on the test plate 16, to avoid a backward transfer of the test plate.

FIG. 9 is a plan view showing the upperstream of the transfer route 7 and the opening of the ascending elevator. A test plate 16 is lifted by the elevator 5 to the cover level 22 of the transfer route and pushed by an air cylinder device 32 to be shifted horizontally on the transfer route, where 32a is an air cylinder, 32b is a cylinder piston, and 32c is a test plate pusher affixed to the piston.

In the figure, 33 is a driving motor for moving the assembly of the magnetic bars 24 alternatingly in the direction indicated by the arrow with a given frequency. The motor 33 drives the joined assembly of the magnetic bars 24 in the alternating directions by means of an eccentric cam mechanism.

Figure 10:
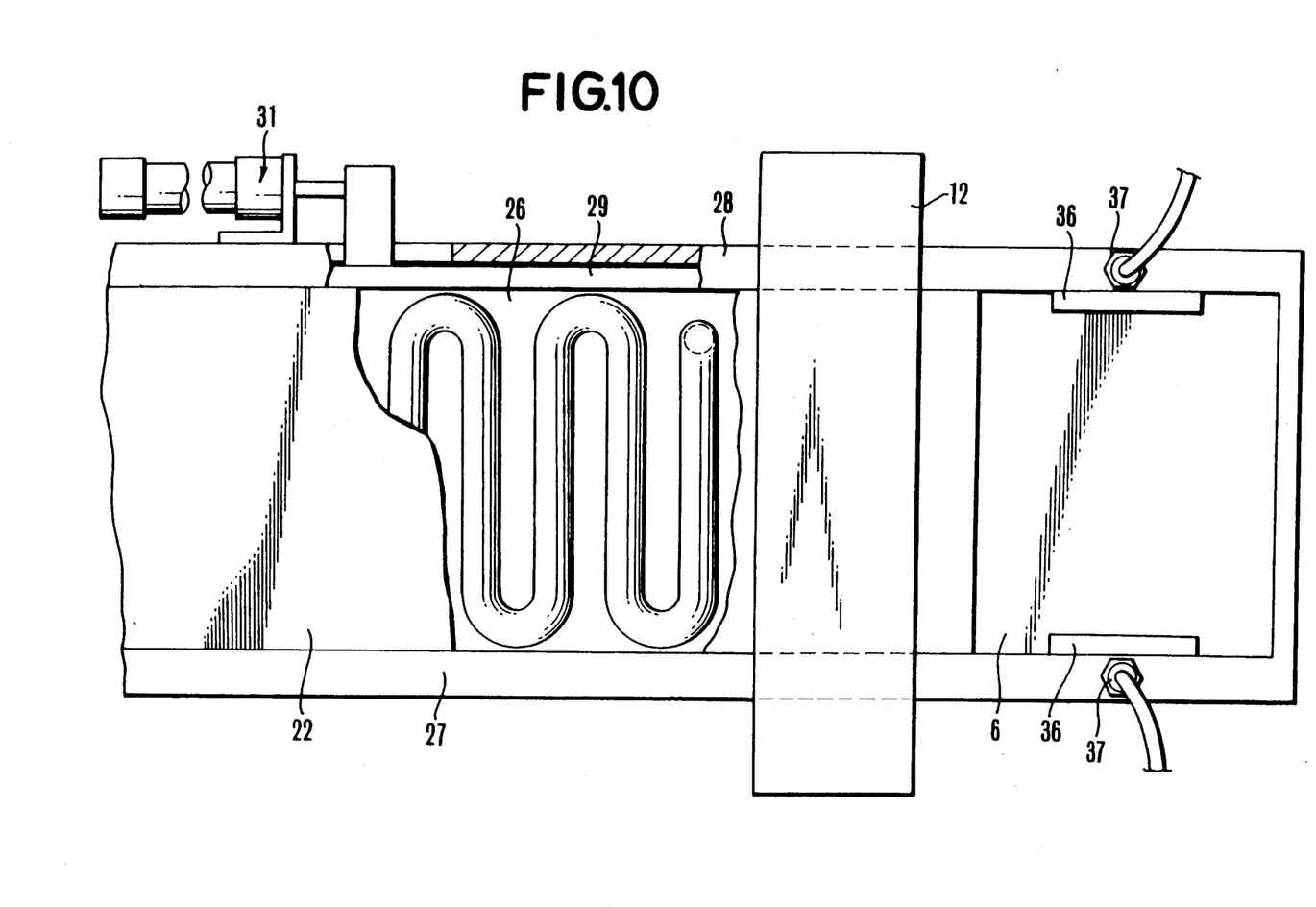
FIG. 10 is a corresponding plan view in the downstream.

FIG. 10 is a plan view showing the downstream of the transfer route 7 and the opening of the descending elevator. The test plates which have completed the optical measurement with a photometric device 12 are transported by the descending elevator to the test cup storage 2 indicated in FIG. 3.

A test plate, when it enters the descending elevator, is first supported by gates 36 on both ends. The gates are then removed by the air cylinder device 37 to free the test plate for the following descent.

In the automatic apparatus thus composed, a test plate having a desired number and combinations of test cups mounted on it is first lifted upward by the ascending elevator 5 to the level of the transfer route 7 and then pushed onto the upperstream of the transfer route 7 by the pushing cylinder device 32. The plate is then shifted intermittently toward the downstream end by a definite pitch by the action of ratchet nails 31 with a predetermined interval of time.

The outline of the whole flow of treatment is explained by a block diagram in FIG. 5(a).

In the next place, component apparatuses disposed on the transfer route 7 are explained.

In this example, a test plate is transferred and stopped at the seal breaking device 8, where a row (a line perpendicular to the direction of transfer) of test cups are pressed downwards by a series of vertically moveable wedges to break their seals. A wedge is provided for a row of test cups and the breaking can be done all at once with a row of test cups. The procedure is repeated for the next row of test cups. A pitch of the intermittent transfer of test cups is equal in magnitude to an interval of the rows of test cups mounted on the test plate.

A test cup whose seal has been broken is transferred to the sample injection device 9 and a certain sample solution is injected successively to the test cups from a nozzle which moves scanningly over the row. The test cups 17 of this example contain in them the magnetic beads 34 with which surface an antibody is combined and another antibody labelled with an enzyme. On the sample solution being injected, a specific reaction of solid antibody-antigen-enzyme labelled antibody is given rise to. This reaction requires a certain period of time and, for the reason, an incubation region of a predetermined length is given to the transfer route 7 as shown in FIG. 2.

Figure 11:
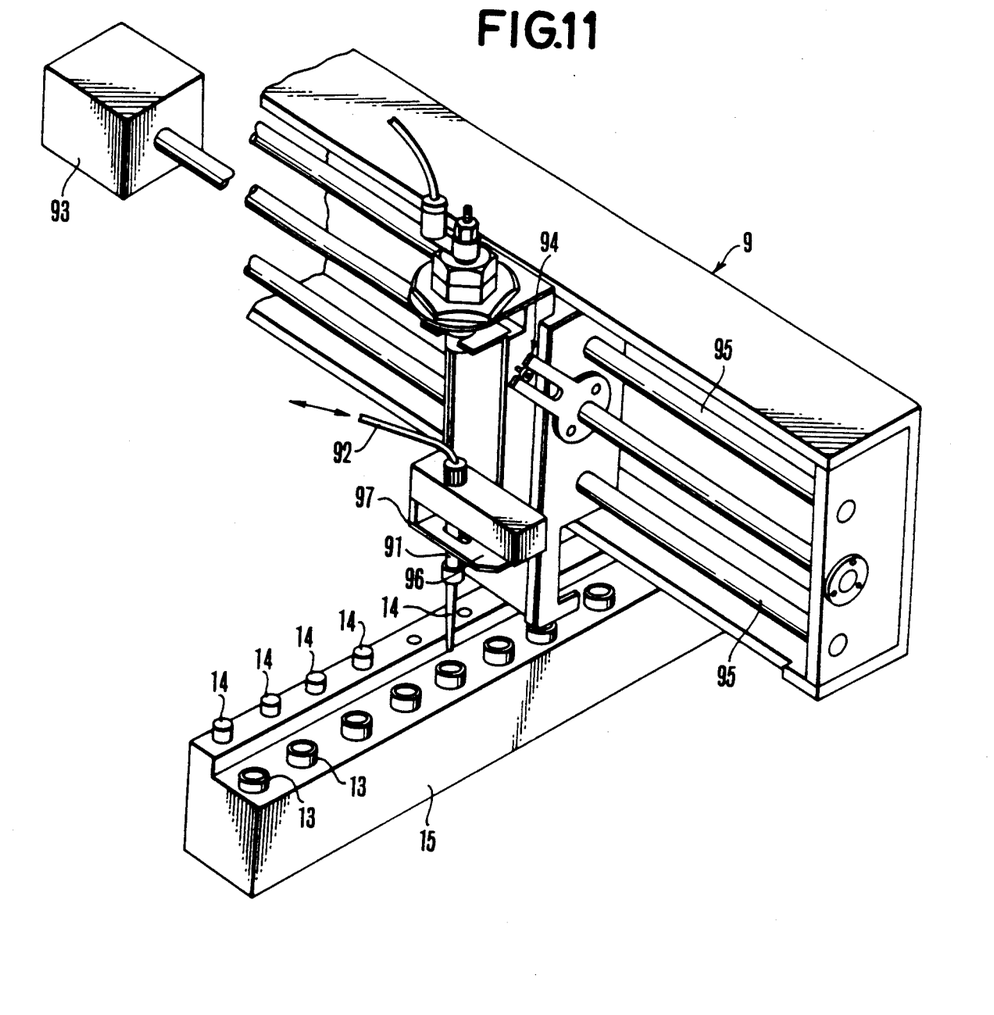
FIG. 11 is a slant view showing an example of a sample injection device and FIG. 12 shows an example of constitution of a B/F separation apparatus and a substrate injection apparatus.

FIG. 11 shows an example of embodiment of the sample injection device 9. On the sample injection device 9, a pipet 91 to whose lower end a nozzle tip 14, which is disposable and each used for a single sample, can fit is connected its the upper end with an air pressure applier (not shown in the figure) via an air pipe 92. The pipet 91 is moved up and down by the drive of a pulse motor 93 via a cam mechanism 94, to suck and inject a sample successively.

The sample injection device 9 of this example injects the sample solution from a single pipet 91 to rows of test cups 17 mounted on a test plate 16. Therefore a mechanism is provided for the pipet 91 to scan the rows guided by the rods 95, though not shown in the figure. The used nozzle tips may, for example be returned to cup holder 15. Of course it may be appreciated that since the pipet can scan along rods 95 and can move up and down, it can be positioned over the nozzle tips 14 in the holder 15 and moved vertically for attaching and detaching the nozzle tips thereto.

A lever 96 is provided to remove the nozzle tips 14. The lever rotates downwards about a fulcrum 97 by the action of a cylinder device (not shown in the figure).

During the period in which the incubation region is passed, the reaction is completed in the test cups. The test plate mounting the test cups is transferred to the B/F separation device 10. While they are intermittently stopped and moved, a washing solution is injected and sucked for the B/F separation and washing with a nozzle which is provided for a row of test cups.

Figure 12:
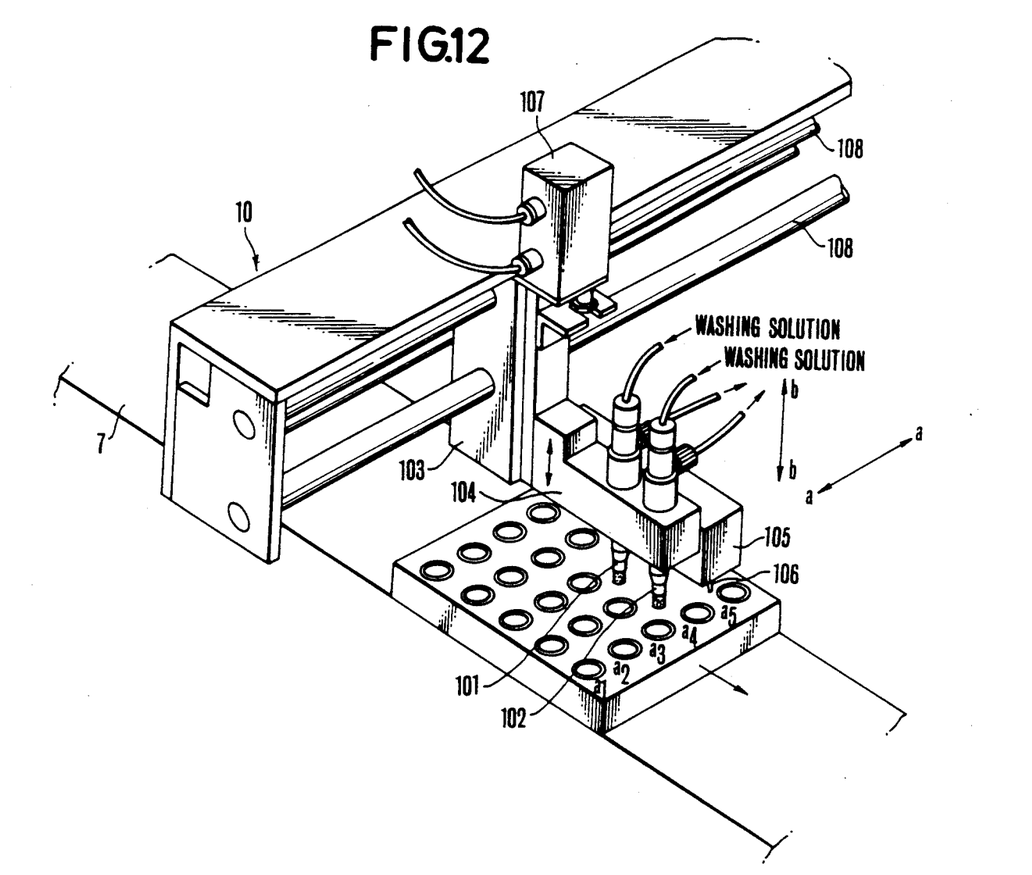

An embodiment of the B/F separation device of this example is shown in FIG. 12. In the present example, the device is combined mechanically with the substrate injection device 11 of the next step.

In this example, a pair of washing tubes 101 and 102, each consisting of an inlet and an outlet tubes of a washing solution, are supported by a supporter 104 which in turn is supported by a supporting frame 103 in such a manner as to permit a vertical movement. A substrate solution reservoir block 105 provided with a thermostat mechanism for maintaining the substrate at a controlled temperature and a substrate solution injection tube 106 are fixed to the supporting frame 103.

The supporter 104 is moved by a horizontal movement of the supporting frame 103 in the direction a—a as shown in FIG. 12, followed by a vertical movement of the supporter 104 in the direction b—b in the figure, so that the washing tubes exactly face the test cups 17 mounted on the intermittently moving test plate 16 to conduct the scheduled washing and the injection of the substrate solution.

The procedure described in the above example enables the washing to be carried out completely and substantially no trace of the free residue of the complex of enzyme labelled antibody to be left unreacted. Therefore, the procedure in this example is useful to improve the accuracy and precision of measurement.

A guide rod 108 is provided to guide movement of the supporter 104 in the direction a—a by an unindicated driving means and an air cylinder device 107 is for transferring the supporting frame 104 in the direction b—b.

Figure 13:
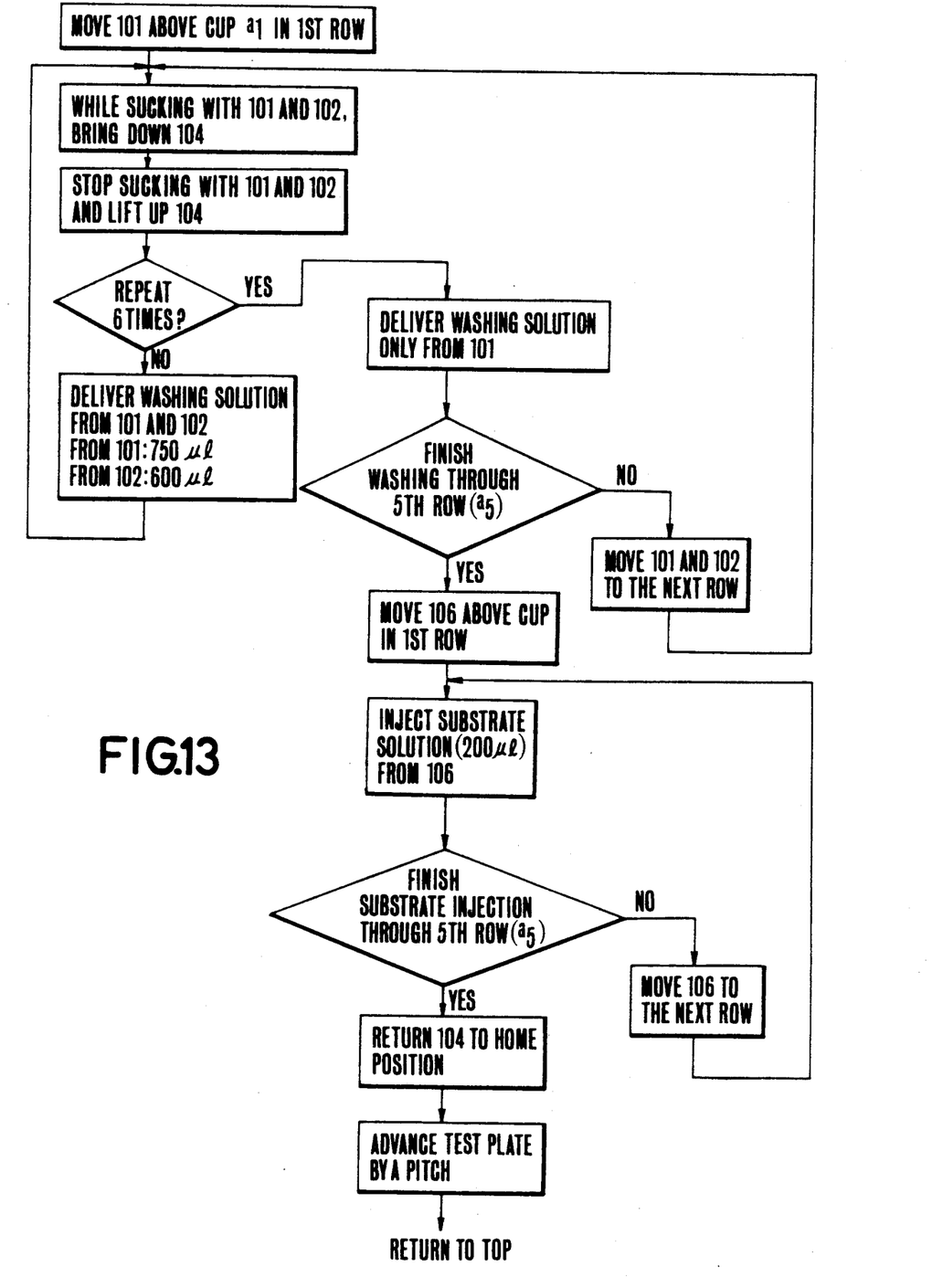
FIG. 13 contains a flow chart explanatorily showing the B/F separation and the substrate injection.

FIG. 13 is a flow chart showing the activity of the subcontroller module 61 which controls the drive of the B/F separation device 10.

By the procedure outlined above, the substrate solution is injected into every test cup in a row and the immunological reaction is initiated.

The substrate solution together with the test cup is transferred to the position of the photometric device 12, stopped for a while during which period a changed state of the substrate is measured optically and the concentration of antigen in the sample is estimated from the information obtained therefrom.

Figure 14:
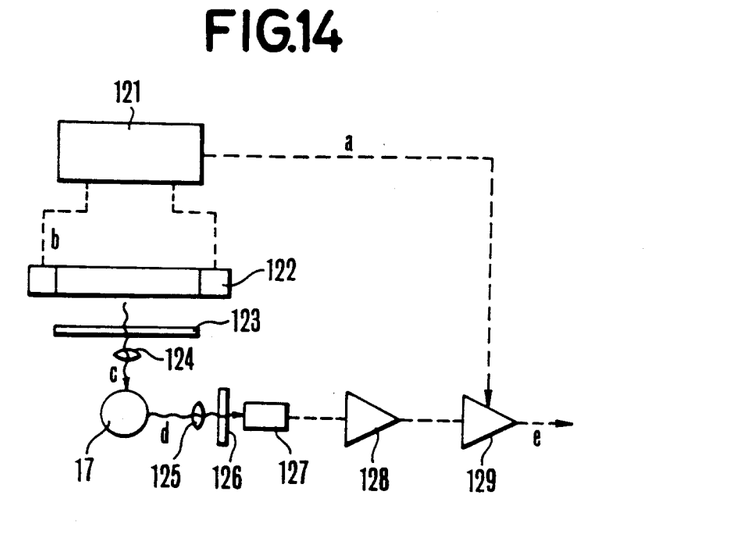
FIG. 14 is a schematic diagram for explaining an example of a fluorescence detecting apparatus and FIG. 15 is a diagram for explaining another example of the substrate injecting apparatus.

Any known photometric apparatus can be applied to the present purpose of the immunological measurement. FIG. 14 is a schematic diagram showing the constitution in principle of the photometric device. In the figure, light is projected in the horizontal direction toward the test cup for the sake of convenience in illustration, but in actual apparatus of this example this is done in the vertical direction.

In this figure, 121 is a pulse voltage power source circuit with a built-in clock pulse generator, and 122 is a fluorescent lamp to which voltages are applied in pulses and therefore the lamp is intermittently lighted with a predetermined frequency so as to avoid the possible disturbance from ordinary fluorescent lamp irradiation. The light from the fluorescent lamp 122 is irradiated in the test cup 17 via the exciting light filter 123 and the focusing lens 124. Thus, a light projecting system is composed.

The fluorescence emitted from a test cup 17 to outside travels through the focusing lens 125 and the fluorescent light filter 126 and is caught by the receiving sensor 127. Electrical signals produced by the characteristics of the receiving sensor 127 are put in a synchronous detector 129 via an amplifier 128. The synchronous detector 129 receives clock pulse signals emitted from the clock pulse generator in the pulse voltage power source circuit 121 and synchronously detects signals from the amplifier 128. Thus, the excited fluorescence components in the test cup 17 can be detected to effectively remove the influences of ordinary light, dark current, and offset components. The signals thus observed are put in a voltmeter (not shown in the figure) and measured, for instance, as variation of fluorescence intensity in a certain interval of time, to be data from which to estimate the amount of the antigen-antibody complex in the sample vessel. The system to measure the received light is composed as mentioned above.

The number of photometric units installed in this example is equal to the number of test cups in a row. However, if there is any restriction with regard to the space of arrangement, the number of photometric units may be reduced to a half and after a measurement is finished the whole photometric units are shifted by the distance between two adjacent test cups before a next measurement is made. In this way, the measurement of a whole row of the test cups may be done in twice repeated operations.

A test plate with which the estimation is completed is transferred via the descending elevator to the test plate storage 3 and is stored for instance on a shelf for those which have passed the measurement.

In this example, test cups 17 mounted on a test plate 16 which is transferred to the descending elevator 6 are automatically picked up from the test plate 16 by a cup disposer device 80 and discarded through a disposer shoot 81 into a disposer basket 70.

An alternative to the mentioned cup disposer device 80 is, for example, a series of fork-shaped cup hangers of which each one picks up a cup and hangs it as the test plate 16 mounting the cups moves closer. The cups remain hung when the test plate moves downwards. The test cups in the hung state are pushed and dropped into the disposer basket 70 by a next test plate coming on its way.

Using the constitution mentioned above, a plurality of test plates can be transferred almost continuously without significant intervals and a high efficiency could be obtained.

Further, when oscillating magnetic bars are provided in the base of the transfer route for the purpose of oscillating the magnetic beads 34 ceaselessly in the test cups at a low frequency as it is done in this example, the reaction between the antigen and the antibody is accelerated and the enzymatic activity works more effectively onto the substrate, and thus the high precision and accuracy in the measurement is attained.

Furthermore, mounting test cups on the test plate can be automatically done in the test cup storage according to a predetermined program, to perform completely automatic measurement substantially without human attendance. This apparatus is proud of very high practical utility because of being a system of high completeness.

The present invention can of course be realized in many kinds of embodiments not restricted to the above examples.

Figure 15:
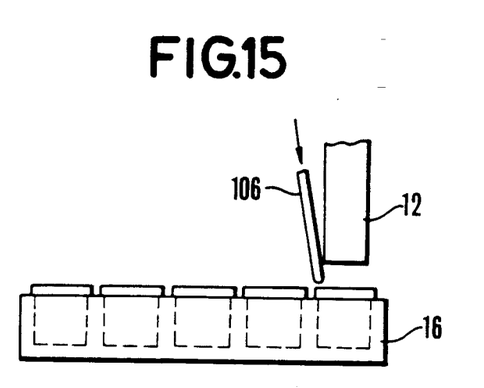

For instance, the B/F separation apparatus and the substrate injection apparatus may be formed separately with merit, as explained by FIG. 15. In this figure, in contrast with the apparatus in FIG. 12, injection of a substrate solution is done to the test cup 17 immediately facing the photometric device 12. In this way, the fluorescence of the substrate in the injected solution can be measured for the change of intensity from the very initial stage and this is especially useful for measuring high concentration samples.

As has been described above, the automated immunoassay analyzer of the present invention can exhibit high practical utility as an automatic system for the enzymatic immunoassay, in that it enables realization of high precision measurements of many samples in continuous and efficient treatments.

What is claimed is:

1. An automated enzyme-immunoassay analyzer comprising:
    a measuring part having a transfer route on which test plates each having a plurality of upwardly opened immunological reaction chambers are transferred during a constant interval of time, and at least means A, B, C and D described below which are arranged on the transfer route from an upstream end to a downstream end of the transfer route in the direction of transfer and in the order referred to:
    A: means for injecting a sample to be assayed into immunological reaction chambers,
    B: means for Bound/Free separation for removing reaction residue in immunological reaction chambers,
    C: means for injecting a substrate solution into the immunological reaction chambers, and
    D: means for photometry with which to measure optically detectable changes caused in a substrate in the immunological reaction chambers,
    in which the means for Bound/Free separation and the means for injecting a substrate solution comprise:
    a horizontally driven support,
    at least one vertically driven washing tube connected to a source of washing liquid and supported by the support,
    a temperature controllable solution reservoir block fixed to the support and comprising thermostatic means for holding and maintaining the substrate solution at a controlled temperature,
    at least one substrate injection tube extending downwardly from an underside of said solution reservoir block, whereby the substrate solution may be discharged from said reservoir block to said immunological reaction chambers at the controlled temperature,
    said washing tube and said substrate solution injection tube being spaced from each other in a direction of pitch of the immunological reaction chambers;
    said analyzer further comprising:
    a test cup storage area located below said measuring part;
    ascending and descending elevators respectively associated with the upstream and downstream ends of said transfer route and respectively connecting said upstream and downstream ends of said transfer route with said test cup storage area for respectively circulating test plates between said transfer route and said test cup storage area.

2. The analyzer of claim 1 including a pick up device in said test cup storage area, said pick up device having means movable for selectively picking up test cups at predetermined locations, and automated control means for controlling movement of said pick up device.

3. The analyzer of claim 1 including:
    an upstream air cylinder device positioned for pushing a test plate from said ascending elevator to said upstream end of said transfer route; and
    air cylinder operated gate means positioned at said downstream end of said transfer route for temporarily supporting a test plate during a transfer of the test plate from said transfer route to said descending elevator.

4. The analyzer of claim 3, including:
    a discarded test cup basket; and
    test cup disposal means for transferring test cups in a test plate at the downstream end of said transfer route to said discarded test cup basket.

5. The analyzer of claim 1, wherein said transfer route includes:
    a transfer plane upon which test plates rest;
    magnet holder positioned below said transfer plane and having grooves extending in the transfer direction;
    magnetic bars fitted in said grooves of said magnetic holder;
    means for reciprocating said magnet bars in said grooves of said magnet holder; and
    a thermostatic heating plate for heating said transfer plane.

6. The analyzer of claim 5 including:
    a plurality of the test plates having ratchet teeth; and
    means for moving said test plates along said transfer route from the upstream end to the downstream end thereof, comprising a transferring bar having ratchet nails fittable int he ratchet teeth of the test plates, and means for reciprocating said transferring bar in said transfer direction, whereby engagement between said ratchet nails and said ratchet teeth moves said test plate.

* * * * *